(12) United States Patent
Zollinger et al.

(10) Patent No.: US 8,122,780 B1
(45) Date of Patent: Feb. 28, 2012

(54) EXPLOSION PROOF VEHICLE FOR TANK INSPECTION

(75) Inventors: William T. Zollinger, Idaho Falls, ID (US); Kerry M. Klingler, Idaho Falls, ID (US); Scott G. Bauer, Idaho Falls, ID (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 1014 days.

(21) Appl. No.: 12/051,952

(22) Filed: Mar. 20, 2008

(51) Int. Cl.
*G01N 33/00* (2006.01)
(52) U.S. Cl. ....... 73/865.8; 73/866.5; 114/312; 114/382
(58) Field of Classification Search ........................ 73/37
See application file for complete search history.

(56) References Cited

U.S. PATENT DOCUMENTS

| | | | | |
|---|---|---|---|---|
| 5,819,863 | A | * 10/1998 | Zollinger et al. | 180/6.5 |
| 5,947,051 | A | * 9/1999 | Geiger | 114/313 |
| 2007/0204675 | A1 | * 9/2007 | Herzog et al. | 73/37 |

* cited by examiner

*Primary Examiner* — Hezron E Williams
*Assistant Examiner* — Gregory J Redmann
(74) *Attorney, Agent, or Firm* — Michael J. Dobbs; Daniel D. Park; John T. Lucas (57) ABSTRACT

An Explosion Proof Vehicle (EPV) having an interior substantially filled with an inert fluid creating an interior pressure greater than the exterior pressure. One or more flexible tubes provide the inert fluid and one or more electrical conductors from a control system to the vehicle. The vehicle is preferably used in subsurface tank inspection, whereby the vehicle is submerged in a volatile fluid.

21 Claims, 8 Drawing Sheets

EXPLOSION PROOF VEHICLE FOR TANK INSPECTION

GOVERNMENT INTERESTS

The United States Government has rights in this invention pursuant to Contract No. DE-AC07-05ID14517, between the U.S. Department of Energy (DOE) and Battelle Energy Alliance.

FIELD OF THE INVENTION

The present invention relates to an Explosion Proof Vehicle. Preferably, the present invention relates to an Explosion Proof Vehicle for in-situ inspection of a subsurface tank containing a volatile fluid, the vehicle being submersible in the volatile fluid.

BACKGROUND OF THE INVENTION

Subsurface tanks containing volatile fluids must be periodically inspected for safety. As the tanks contain volatile fluid, care must be taken to prevent any electrical charges or even relatively small amounts of light from entering the tank while the volatile fluids are present. Consequently, to inspect subsurface storage tanks the tanks are generally first drained, cleaned and ventilated and then, visually inspection by inspection personnel.

Current methods of inspecting tanks such as those which enclose petroleum or other caustic chemicals, especially large tanks, are very expensive, generally costing more than $250,000 depending upon the size of the tank. Unfortunately, the tank is rendered unserviceable for a month or more as the tank is drained, ventilated and thereafter inspected. Worse yet, many subsurface tanks are inadequately tested due to the complexity and cost of testing, increasing the risk of severe safety concerns to the environment and personal in the area, as well as contamination of the tank contents.

U.S. Pat. No. 5,819,863, hereby fully incorporated by reference, describes a vehicle capable of operating in a volatile fluid. This vehicle uses wheels magnetically coupled to a metal tank. In an emergency, the wheels are magnetically decoupled from the tank, and a retrieval balloon, filled by an inert gas from a pressurized gas container within the vehicle, increases the buoyancy of the vehicle, and therefore propelling it upwards. The interior of the vehicle is pressurized with an inert gas to prevent an internal explosion. In the event of a leak, the inert gas will flow outward, into the volatile fluid and the vehicle will power off to prevent explosion. Unfortunately, once a leak occurs in the vehicle and the vehicle is powered down, it must be manually extracted. Generally, this will require the user to physically pull the vehicle up by its cabling. Furthermore, the exposure of the interior components of the vehicle to the volatile fluid, even if the vehicle is powered down, may be detrimental, posing safety risks or causing undesirable reactions such as corrosion of the interior components.

Unfortunately, the vehicle described in U.S. Pat. No. 5,819,863 may get stuck under various obstacles within the tank, whereby the vehicle must be abandoned or physically extracted by the operator, generally by dismantling the tank. Furthermore, the vehicle described in U.S. Pat. No. 5,819,863 uses magnetically coupled wheels, making the vehicle unusable in non-magnetic tanks. The magnetically coupled wheels limit the operator's perspective, which may be optimal when the vehicle is unattached from the tank wall.

Other attempts have been made to create a vehicle for tank inspection, however these vehicles generally do not have measures to prevent explosion creating severe safety risks when used in explosive environments if the tank is not completely emptied and vented before inspection.

Unfortunately, current devices and methods for the inspection of volatile tanks are cost prohibitive and time consuming, leading to sever safety risks. Although there has been some progress with in-situ, subsurface tank inspection vehicles, current devices and methods have been ineffective due to a lack of versatility and reliable extraction.

SUMMARY OF THE INVENTION

An Explosion Proof Vehicle (EPV) having an interior and an exterior. The interior is substantially filled with an inert fluid and maintained at a pressure greater than the exterior pressure. One or more flexible tubes provide the inert fluid and one or more electrical conductors from a control system to the vehicle. The vehicle is preferably used in subsurface tank inspection, whereby the vehicle is submerged in a volatile fluid.

One embodiment of the present inventions provides a means for tanks storing volatile fluid to be inspected by a device which may be submerged in the volatile fluid and capable of inspecting the tank for conditions which could potentially impair the integrity of the tank without the need to drain the tanks contents.

DETAILED DESCRIPTION OF THE INVENTION

An Explosion Proof Vehicle (EPV) having an Interior and Exterior. The Interior is substantially filled with an Inert Fluid creating an Interior Pressure greater than the Exterior Pressure. One or more Flexible Tubes provides the Inert Fluid and one or more Electrical Conductors from a Control System to the Vehicle. The Vehicle is preferably used in subsurface Tank inspection, whereby the Vehicle is submerged in a Volatile Fluid.

One embodiment of the Vehicle comprises a Control System, a Moving Means, a Pressure Controlling Means, a Transmitting Means, a Receiving Means and a Spark Reducing Means. The Pressure Controlling Means creates and maintains the Interior pressure of the Vehicle using an Inert Fluid supplied by a Supply Means. The Spark Reducing Means minimizes sparking at the Exterior of the Vehicle, for example sparking between the Vehicle and a Tank. The Transmitting Means transmits a signal which is received by the Receiving Means and used to provide information about the area surrounding the Vehicle.

Figure 1:
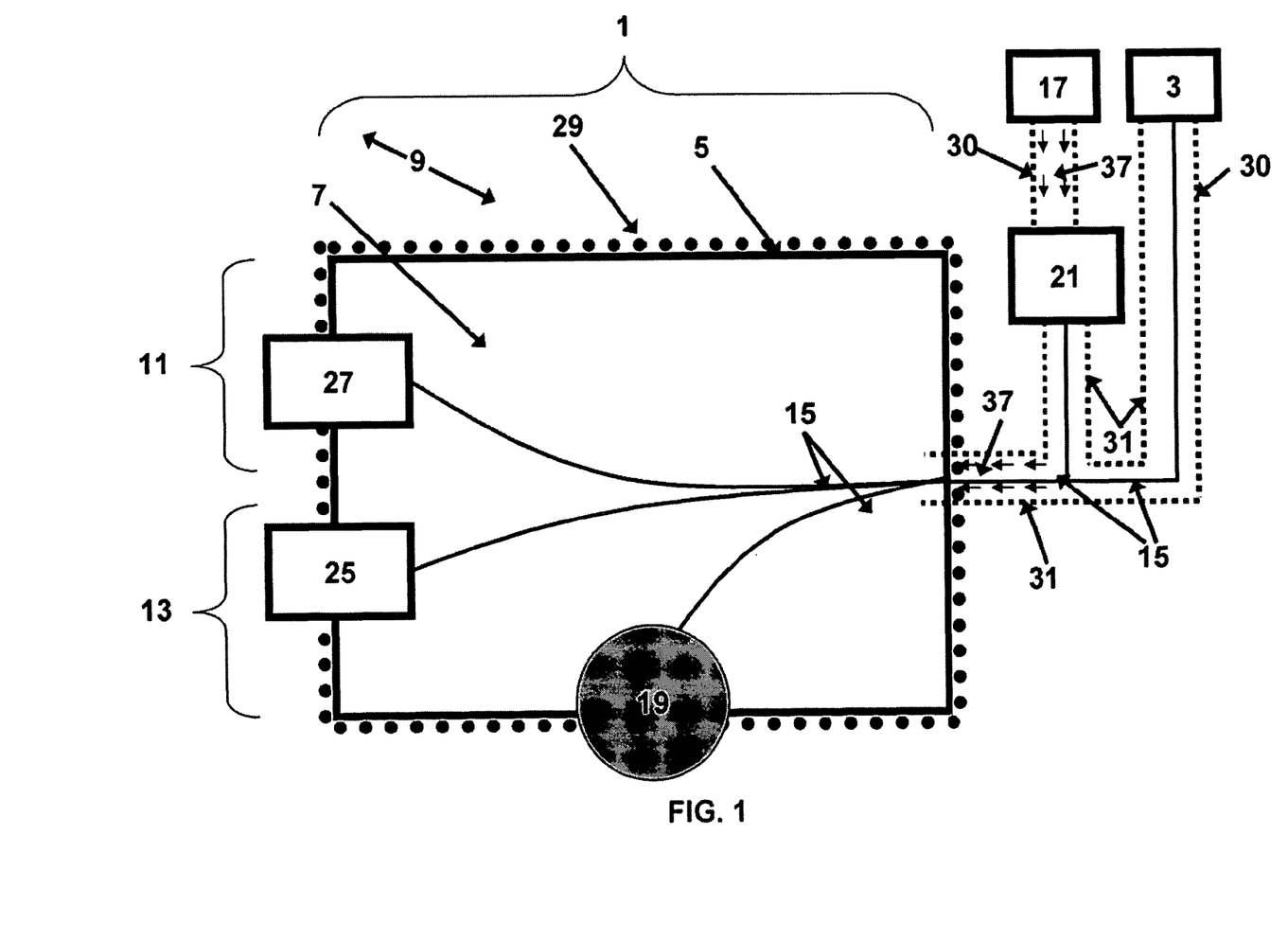
FIG. 1 depicts a block diagram of one embodiment of an Explosion Proof Vehicle.
Figure 2:
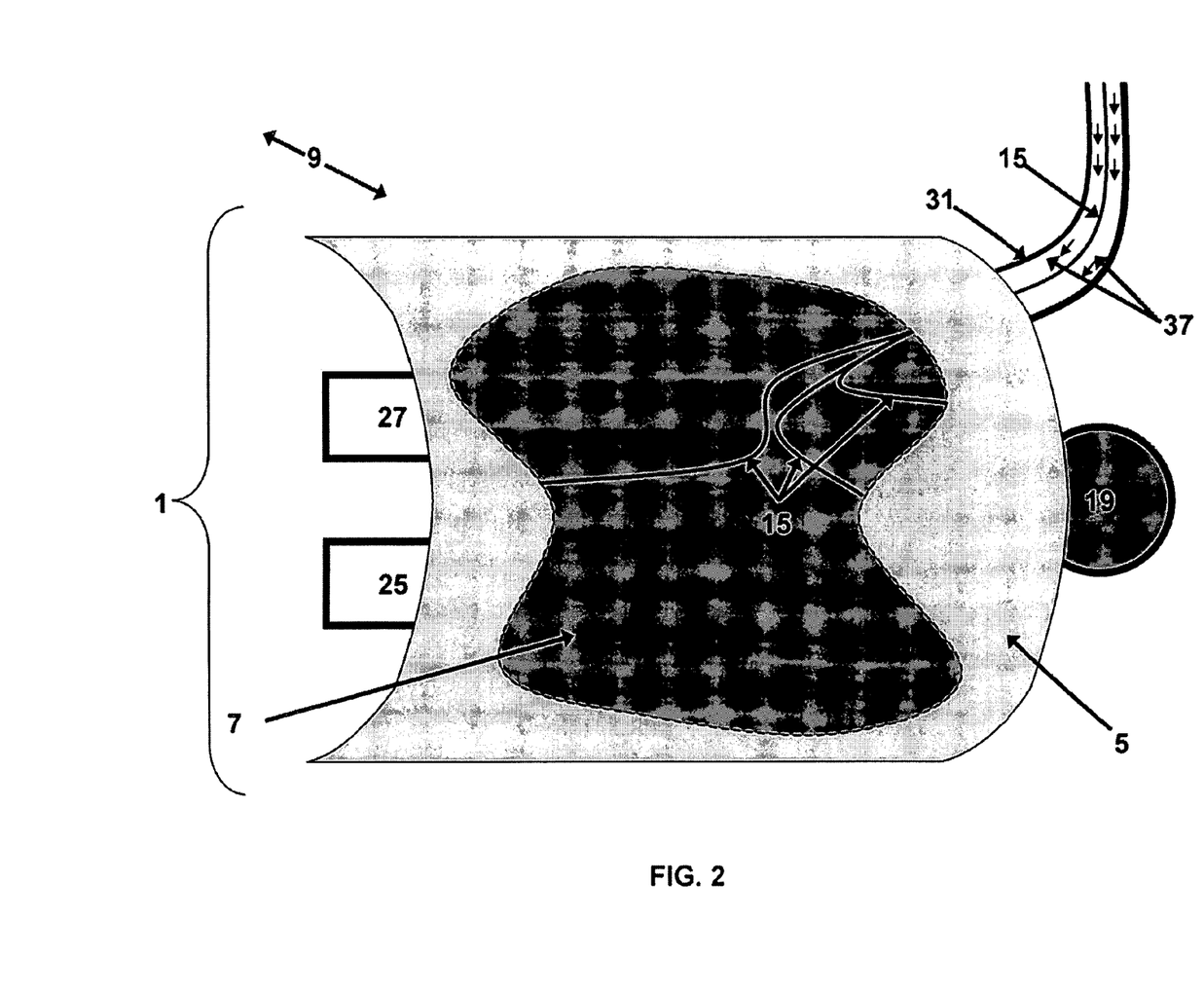
FIG. 2 depicts a cut-out view of one embodiment of an Explosion Proof Vehicle having a cutout showing interior components.

FIG. 1 and FIG. 2

FIG. 1 and FIG. 2 depict one embodiment of an Explosion Proof Vehicle 1. In this embodiment, the Vehicle 1 comprises an Outer Shell 5 having an Interior 7 and an Exterior 9, as well as a Top 11 and a Bottom 13. A Moving Means 19 is connected to the Bottom 13 of the Outer Shell 5. One or more Electrical Conductors 15 electrically connect a Control System 3 to the Moving Means 19, a Transmitting Means 25 and a Receiving Means 27. A Supply Means 17 supplies an Inert Fluid 37 through one or more Supply Tubes 30 to a Pressure Controlling Means 21. The Pressure Controlling Means 21 is connected through one or more Flexible Tubes 31 to the Outer Shell 5, passing the Inert Fluid 37 to the Interior 7 of the Vehicle 1. The Pressure Controlling Means 21 maintains the pressure of the Interior 7 above the pressure of the Exterior 9. Electrical discharges between the Outer Shell 5 and the Exterior 9 are minimized by a Spark Reducing Means 29.

Figure 3:
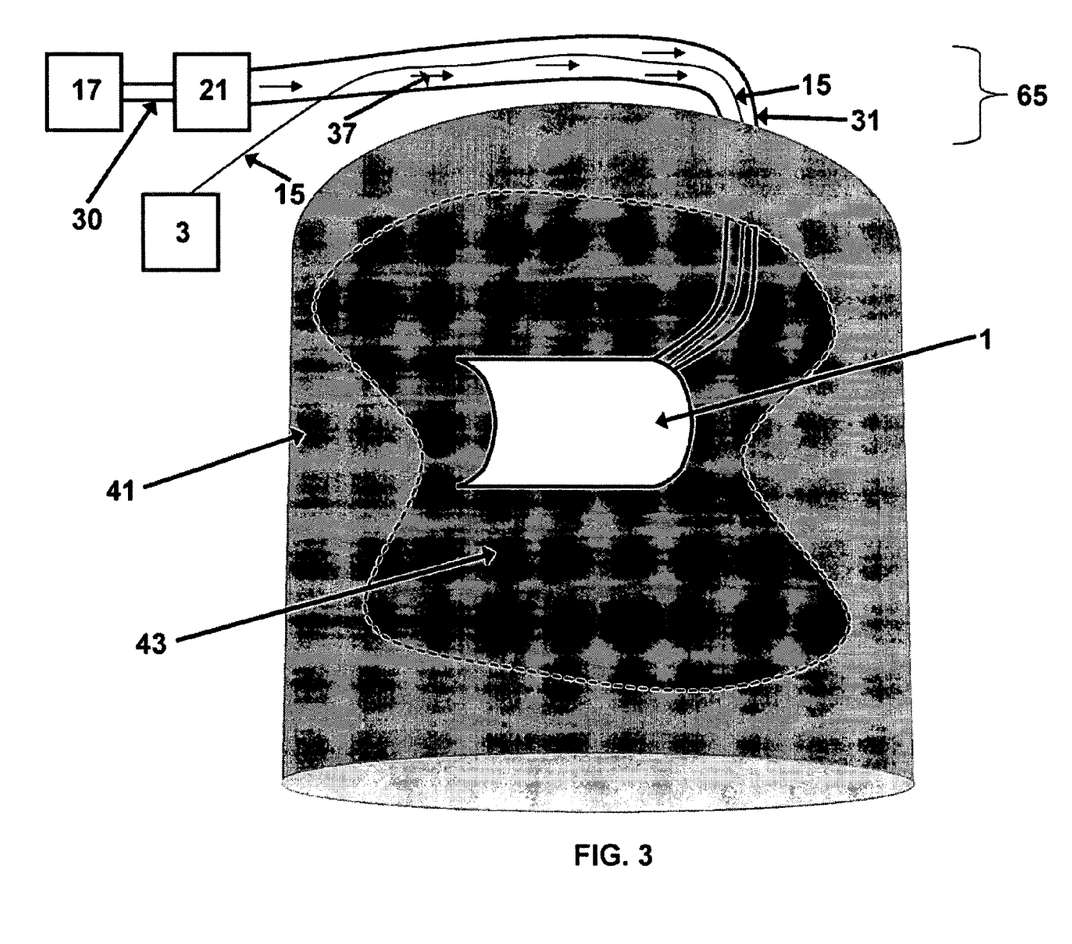
FIG. 3 depicts a cut-out view of one embodiment of the Explosion Proof Vehicle in a Tank having a Volatile Fluid.

FIG. 3

FIG. 3 depicts a preferred usage of submerging the Vehicle 1 shown in FIG. 1 and FIG. 2 in a Tank 41 having a Volatile Fluid 43. The one or more Flexible Tubes 31 contain the Inert Fluid 37 and the one or more Electrical Conductors 15 for operating the various electronics in the Vehicle 1. Preferably, the Tank 41 is buried underground.

In the embodiment shown in FIG. 3, the one or more Electrical Conductors 15 preferably connect the Control System 3 to the various electronics internal to the Vehicle 1 and pass into the one or more Flexible Tubes 31 at an non-submersed area 65 of the one or more Tubes 31. The non-submersed area 65 is an area of the one or more Tubes 31 which will not be exposed to the Volatile Fluid 43. Therefore the one or more Wires 15 do not have to be designed for use while submersed in the Volatile Fluid 43, which may pose as a serious explosive danger. Preferably, in this embodiment, the one or more Wires 15 pass into the interior of the one or more Flexible Tubes 31 and remain in the interior of the one or more Flexible Tubes 31 until they exit the one or more Flexible Tubes 31 and pass into the Interior 7.

In the alternative, the one or more Wires 15 are designed for submersion within the Volatile Fluid 43 of the Tank 41 and pass into the one or more Tubes 31 while submersed in the Volatile Fluid 43. In yet another embodiment, the one or more Wires 15 are designed for submersion within the Volatile Fluid 43 of the Tank 41 and pass directly into Vehicle 1.

Tank 41

The Tank 41 is any means know in the art to hold the Volatile Fluid 43. Tank 41 material and design depend upon the Volatile Fluid 43. In a preferred embodiment, the Tank 41 is a carbon steel tank having an interior with an epoxy coating. Preferably, the Tank 41 is buried underground and the Volatile Fuel 43 is gasoline.

Volatile Fluid 43

The Volatile Fluid 43 is preferably any fluid that is flammable, explosive, corrosive or a combination thereof. Examples of Volatile Fluids 43 include, but are not limited to, jet fuel, naphtha, gasoline, and diesel, as well others known in the art.

Outer Shell 5

The Outer Shell 5 is preferably any material suitable for submersion in the Volatile Fluid 43. Preferably, the Outer Shell 5 is made of a metal, ceramic or plastic. In a preferred embodiment, the Outer Shell 5 is made of a metal. Preferably, the Outer Shell 5 is optimized to minimize interaction with the Volatile Fluid 43, for example corrosion and explosions.

Preferably, the Outer Shell 5 prevents the Volatile Fluid 43 from passing into the Interior 7, the Inert Fluid 37 from passing into the Exterior 9, or a combination thereof. More preferably, the Outer Shell 5 prevents the Volatile Fluid 43 from passing into the Interior 7 and prevents the Inert Fluid 37 from passing into the Exterior 9. In an alternative embodiment, the Outer Shell 5 has a Sealing Layer which prevents the Volatile Fluid 43 from passing into the Interior 7, the Inert Fluid 37 from passing into the Exterior 9, or a combination thereof.

Pressure Controlling Means 21

The Pressure Controlling Means 21 maintains the Interior 7 of the Vehicle 1 at a pressure above the Exterior 9 pressure of the Vehicle 1. The Pressure Controlling Means 21 uses the Inert Fluid 37 supplied by the Supply Means 17 to maintain the pressure of the Interior 7 of the Vehicle 1 above the pressure of the Exterior 9 of the Vehicle 1. Maintaining a higher Interior 7 pressure of the Vehicle 1 insures that any leakage will occur outwardly into the Exterior 9 instead of the Volatile Fluid 43 dangerously leaking inwards into the Interior 7. Therefore, upon a breach of the Sealing Means between the Interior 7 and the Exterior 9, the Inert Fluid 37 will leak outward into the Volatile Fluid 43.

If the Interior 7 pressure of the Vehicle 1 is allowed to drop below the Exterior 9 pressure of the Vehicle 1, the various components inside the Interior 7 of the Vehicle 1 will need to be designed to avoid interaction with the Volatile Fluid 43. For example, the various components will need to resist any corrosive effects of the Volatile Fluid 43, while also preventing any sparking or heat generation which could cause an explosion in the presence of the Volatile Fluid 43.

Preferably, the Pressure Controlling Means 21 has a means for increasing and decreasing the Interior 7 pressure. As the Vehicle submerges in the Volatile Fluid 43 it may be desirable to increase and decrease the Interior 7 pressure of the Vehicle 1 in relationship to Exterior 9 pressure of the Vehicle 1, as the Exterior 9 pressure of the Vehicle 1 will vary according to the depth of the Vehicle 1 in the Volatile Fluid 43 and density of the Volatile Fluid 43. Preferably, to reduce the Interior 7 of the Vehicle 1, the Inert Fluid 37 is expelled outwardly into the Volatile Fluid 43. In one preferred embodiment, the expelled Inert Fluid 37 is used to help move or stabilize the Vehicle 1. More preferably, to reduce the Interior 7 of the Vehicle 1, the Inert Fluid 37 is recycled back to the Supply Means 17. In a preferred embodiment, the Pressure Controlling Means 21 is a computer (including microcontrollers, field programmable gate array (FPGA), application-specific integrated circuit (ASIC), or other electronic and mechanical calculating means) controlled butterfly valve.

Transmitting Means 25

The Transmitting Means 25 produces a signal which is received by the Receiving Means 27. Preferably, the signal produced by the Transmitting Means 25 is generated at the Vehicle 1, but in the alternative, the signal is produced outside of the Vehicle 1. Preferably, the Transmitting Means 25 is a light source, a radio frequency source, a sound source, or a combination there of, as well as any other radiation source. Preferably, the Transmitting Means 25 provides infrared or visible light. Care must be taken to insure the light and any heat generated in the production of the light does not interact with the Volatile Fluid 43. In one embodiment, a low power LED (light emitting diode) is used to generate light, which is detected by the Receiving Means 27. In a preferred embodiment, light is generated outside the Tank 41 and away from the presence of the Volatile Fluid 43 (e.g. the embodiment shown in FIG. 8).

In a preferred embodiment, the Transmitting Means 25 produces an ultrasound signal at the Vehicle 1 which is detected by the Receiving Means 27. In an alternate embodiment, the Transmitting Means 25 produces an ultrasound signal outside the Vehicle 1 which is detected by the Receiving Means 27.

Preferably, the Transmitting Means 25 uses one or more Sonar Transducers electrically connected to Sonar Electronic and flexibly connected to the Vehicle 1 extending outward into the Volatile Fluid 43. The flexibility of the Sonar Transducer allows the Vehicle 1 to pass through tight spaces, for example the entrance hatch of a Tank 41. The Sonar Transducer is preferably made of a material resistant to the Volatile Fluid 43 or more preferably protected using a coating or a sealed apparatus from the Volatile Fluid 43. For example, in a preferred embodiment, the Sonar Transducer is placed in a plastic sheath designed to be resistant to the Volatile Fluid 43, while also minimizing any signal attenuation of the Sonar Transducer. In an alternate embodiment, the Sonar Transducer is coated with a coating resistant to the Volatile Fluid 43, while also minimizing any signal attenuation of the Sonar Transducer.

When the Transmitting Means 25 uses one or more Sonar Transducers, Sonar Electronics preferably generate the signal passed to the Sonar Transducers for the generation of sonar within the Volatile Fluid 43. Preferably, the Sonar Electronics are integrated into the Control System 3, which is connected to the Sonar Transducer by the one or more Wires 15. In the alternative, the Sonar Electronics can be placed in the Interior 7 of the Vehicle 1, however it is preferable to integrate the Sonar Electronics in the Control System 3 in order to reduce the Vehicle 1 size and weight, as well as reduce the risk of exposing the Sonar Electronics to the Volatile Fluid 43.

Receiving Means 27

The Receiving Means 27 is a device capable of detecting the signal generated by Transmitting Means 25. An image of the Volatile Fluid 43, the interior of the Tank 41, or a combination thereof is preferably generated by information from the Receiving Means 27. In a preferred embodiment, light from the Transmitting Means 25 is detected by the Receiving Means 27 and used to construct an image at the Control System 3.

The Receiving Means 27 is preferably a camera, more preferably a CCD camera. Preferably, the Receiving Means 27 is a camera attached to the Vehicle 1, but in the alternative may be a camera exterior to the Vehicle 1. In one embodiment, the Receiving Means 27 is a portable camera submersible in the Volatile Fluid 43.

Preferably, the signal produced by the Transmitting Means 25 is detected by the Receiving Means 27 at the Vehicle 1, but in the alternative, the signal is received outside of the Vehicle 1. In one embodiment, one or more receivers are positioned atop the Tank 41 are used to detect the signals generated by the Transmitting Means 25. In a preferred embodiment, three or more detectors are used to triangulate the location of the Vehicle 1 form a signal produced at the Vehicle 1.

In one embodiment, The Receiving Means 27 is an array of receivers capable of constructing an image of the Volatile Fluid 43, the interior of the Tank 41, or a combination thereof. In a preferred embodiment, the Receiving Means 27 is a 3×3 ultrasound transducer array, which receives a signal produced by the Transmitting Means 25. In this embodiment, a computer (including microcontrollers, field programmable gate array (FPGA), application-specific integrated circuit (ASIC), or other electronic and mechanical calculating means) constructs an image from the signal received by the array. In this embodiment, the computer in real time adds the signals received by the array while taking into account the delay of the signal in the Volatile Fluid 43. Therefore, the signal direction can be determined and an enhanced image (using the aggregate of a ultrasound transducers) can be constructed. Preferably, the frequency, the amplitude, or a combination thereof of the signal is used to construct a colorized image.

Control System 3

The Control System 3 controls the various components of the Vehicle 1. Preferably, the Control System 3 controls the various components of the Vehicle 1 without user intervention, but may require some operator interaction. The Control System 3 is preferably a computer (including microcontrollers, field programmable gate array (FPGA), application-specific integrated circuit (ASIC), or other electronic and mechanical calculating means).

One or More Supply Tubes 30

The one or more Supply Tubes 30 transfers of the Inert Fluid 37 from the Supply Means 17 to the Pressure Controlling Means 21. Suitable Supply Tubes 30 include but are not limited to pipes, tubes, channels, etc. . . .

The one or more Supply Tubes 30 are preferably made out of plastics, ceramics, metals, or combinations thereof. Preferably, the one or more Supply Tubes 30 are rigid, but in the alternative the one or more Supply Tubes 30 may be flexible or have flexible couplings. In yet another embodiment, the one or more Supply Tubes 30 are the same type of tubes as used for the one or more Flexible Tubes 31.

One or More Flexible Tubes 31

The one or more Flexible Tubes 31 allows the transfer of the Inert Fluid 37 from the Pressure Controlling Means 21 to the Vehicle 1, while also transferring various electrical signals from the Control System 3 through the one or more Electrical Conductors 15. Suitable one or more Flexible Tubes 31 include but are not limited to pipes, tubes, channels, etc. . . .

The one or more Flexible Tubes 31 are preferably made so as to not react with the Volatile Fluid 43 or protected using a coating or a sealed apparatus from the Volatile Fluid 43. For example, in a preferred embodiment, the one or more Flexible Tubes 31 are placed in a plastic sheath designed to be resistant to the Volatile Fluid 43. In an alternate embodiment, the one or more Flexible Tubes 31 are coated with a coating resistant to the Volatile Fluid 43, while also minimizing any signal attenuation of the Sonar Transducer. The one or more Flexible Tubes 31 are preferably made out of plastics, ceramics, metals, or combinations thereof. Preferably, the one or more Tubes 31 are flexible, but alternatively may be one or more rigid tubes having flexible couplings.

Supply Means 17

The Supply Means 17 supplies the Inert Fluid 37 into the one or more Supply Tubes 30. The Supply Means 17 is preferably optimized for pumping the Inert Fluid 37.

Inert Fluid 37

The Inert Fluid 37 is a fluid which is not explosive in the environment provided by the Interior 5 of the Vehicle 1 and will not pose as a serious environmental or safety risk when exposed to the Volatile Fluid 43. Preferably, the Inert Fluid 37 is a welding gas, a noble gas, or a combination thereof. In a preferred embodiment, the Inert Fluid 37 is nitrogen or argon, more preferably nitrogen.

One or More Electrical Conductors 15

The one or more Electrical Conductors 15 transfer an electrical signal from the Control System 3 to the various components within the Vehicle 1. Preferably the one or more Electrical Conductors 15 are one or more electrically conductive wires. In the alternative, the one or more Electrical Conductors 15 are any means of transferring the electrical signal, for example electrically conductive channels within the one or more Flexible Tubes 31.

In the alternative, other signals may be used instead of electrical signals, for example light or radio waves may be used to transfer signals from the Control System 3 to the various components within the Vehicle 1. In one embodiment, one or more optical fiber cable, waveguide, light channels, radio frequency channels, electrical channels or a combination thereof are used to transfer signals from the Control System 3 to the various components within the Vehicle 1.

Moving Means 19

The Moving Means 19 is any means known in the art to move the Vehicle 1. Preferably, the Moving Means 19 is one or more wheels, jets, turbines, guides, fins, magnets, etc., or a combination thereof. In one embodiment, the magnetic wheels described in U.S. Pat. No. 5,819,863 are used as the Moving Means 19. In another embodiment, one or more motors connected to one or more turbines on the Exterior 9 of the Vehicle 1 are used to propel the Vehicle 1 in the Volatile Fluid 43. In yet another embodiment, wheels are placed on the Bottom 13 of the Outer Shell 5 allowing the Vehicle 1 to move. In another embodiment, one or more jets expelling the Inert Fluid 37 are used to move the Vehicle 1.

Stepper Motors may be used in a Moving Means 19, the Filling Means 49, or any other component within the Interior 7 of the Vehicle 1. These Stepper Motors may have difficulty operating at distances over 100 ft. To alleviate this problem, the various electronics for the Stepper Motors may be positioned inside the Interior 7. However, it is preferable to position the various Stepper Motor electronics outside of the Vehicle 1 as much as possible to prevent electrical noise and to minimize the Vehicle 1 size and weight.

In a preferred embodiment, the electrical connection between the Stepper Motor Electronic, preferably the Control System 3 and one or more Stepper Motors in the Vehicle 1 are highly conductive electrical conductors. Preferably, the electrical conductors are power conduction cables with a high number of large diameter copper strands. A highly conductive conductor will minimize line loss, increasing the maximum cabling of the system. In one preferred embodiment having 100 feet or more of wires between the Control System 3, one or more wires between the Control System 3 and one or more stepper motors have a diameter of /1;2 an inch or larger.

Spark Reducing Means 29

The Spark Reducing Means 29 reduces the likelihood of an electrical breakdown between the Vehicle 1 and the Tank 41. Preferably the Spark Reducing Means 29 is one or more coatings having brass, bronze, aluminum, TEFLON® or a combination thereof. In a preferred embodiment, the Spark Reducing Means 29 is a TEFLON® coating doped with Carbon.

Figure 4:
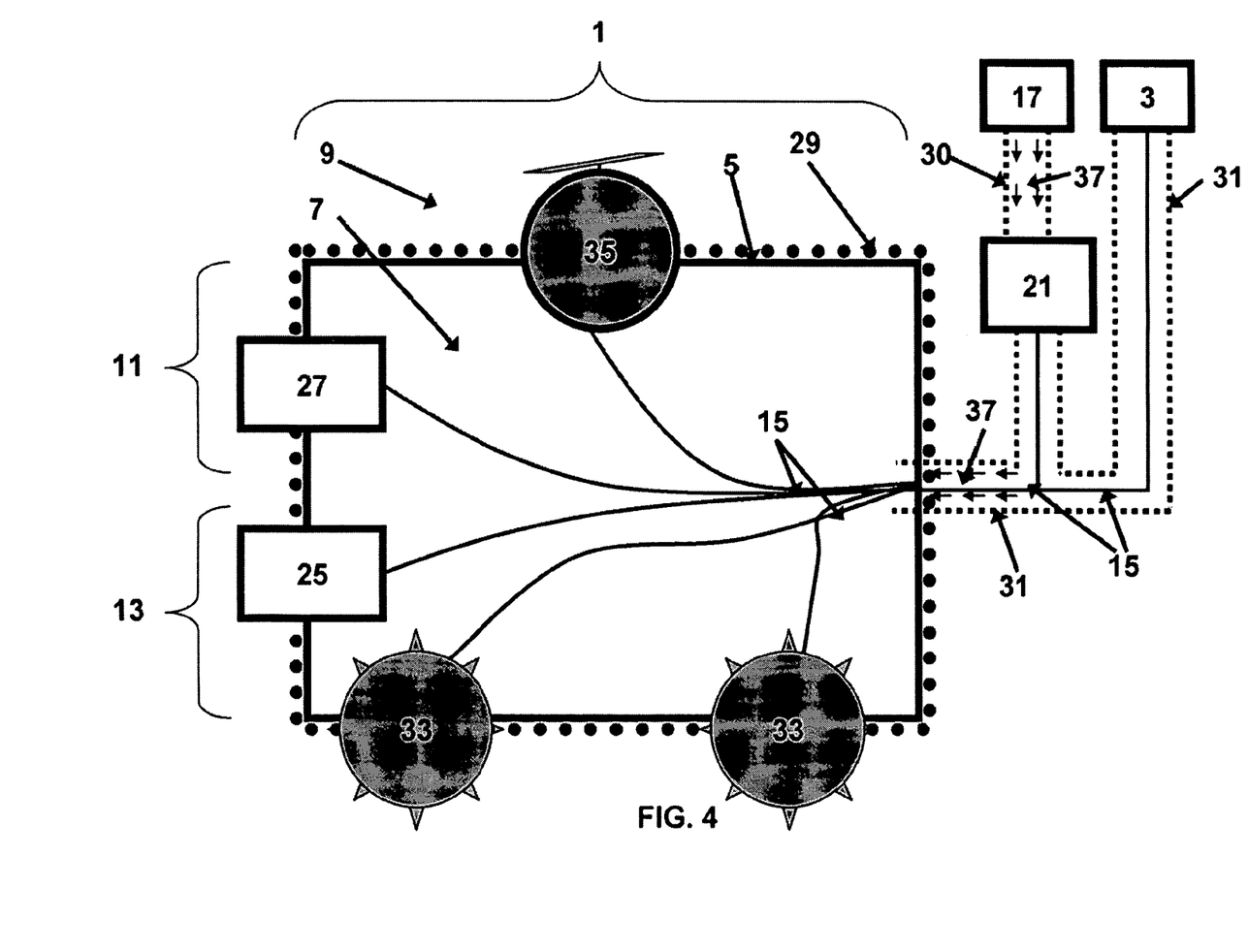
FIG. 4 depicts a block diagram of one embodiment of an Explosion Proof Vehicle using Wheels and one or more Turbines to move the Vehicle.

FIG. 4

FIG. 4 depicts an embodiment similar to the embodiment shown in FIG. 1 with the addition of one or more Wheels 33 placed on the Bottom 13 of the Outer Shell 5 and one or more Turbines 35 placed on the Top 11 of the Vehicle 1. The Turbines 35 apply a force to the Top 11 of the Vehicle 1 having a vector running toward the Bottom 13 of the Outer Shell 5. This allows additional traction to the Wheels 33. As known in the art, one or more jets, turbines, guides, fins, magnets, or a combination thereof may also be used in place of the Turbines 35 to provide addition traction to the Wheels 33. Preferably, the Weeks 33 connect to the Control System 3 via one or more Electrical Conductors 15.

Figure 5:
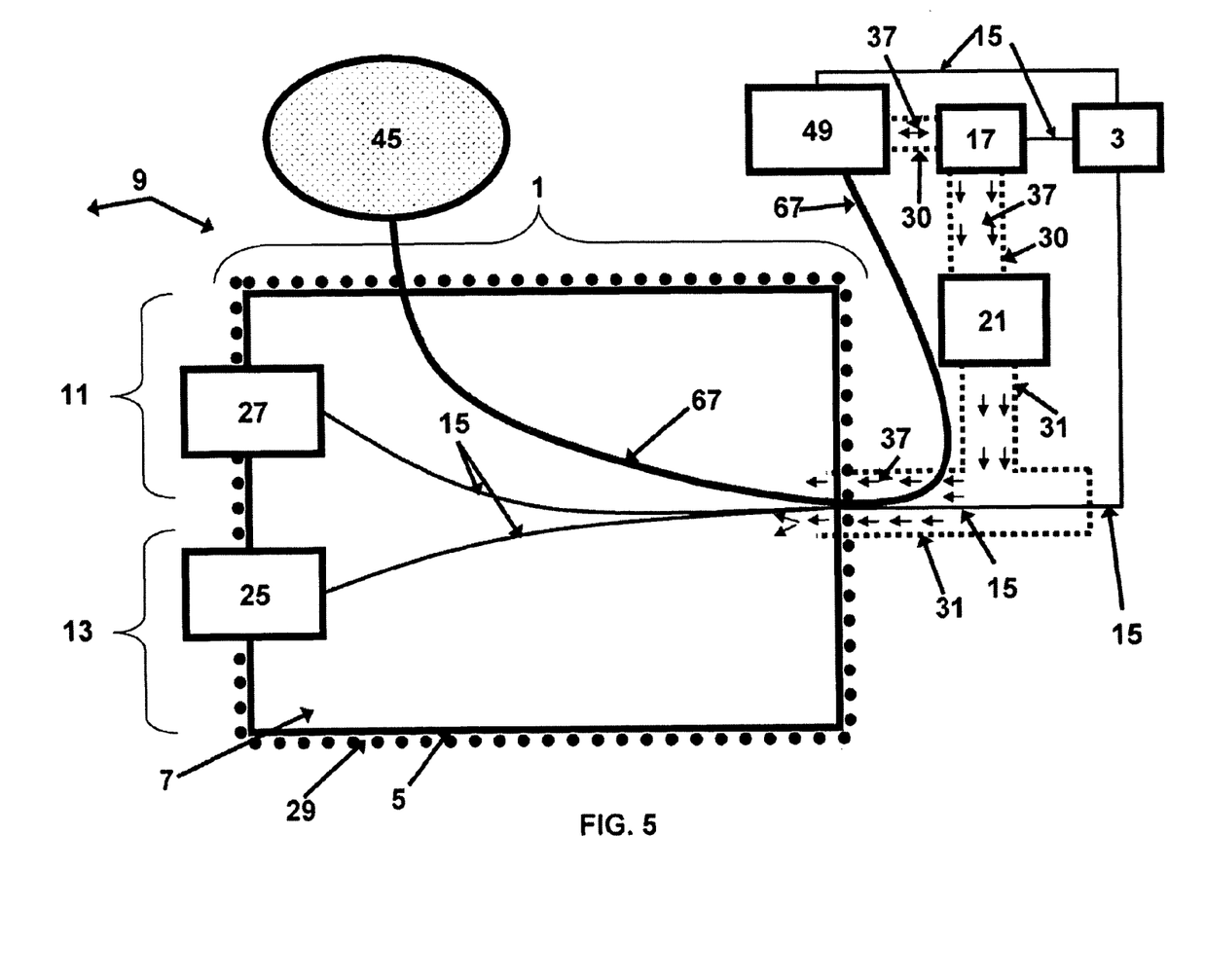
FIG. 5 depicts a block diagram of one embodiment of an Explosion Proof Vehicle using an Inflatable Float to move the Vehicle.
Figure 6:
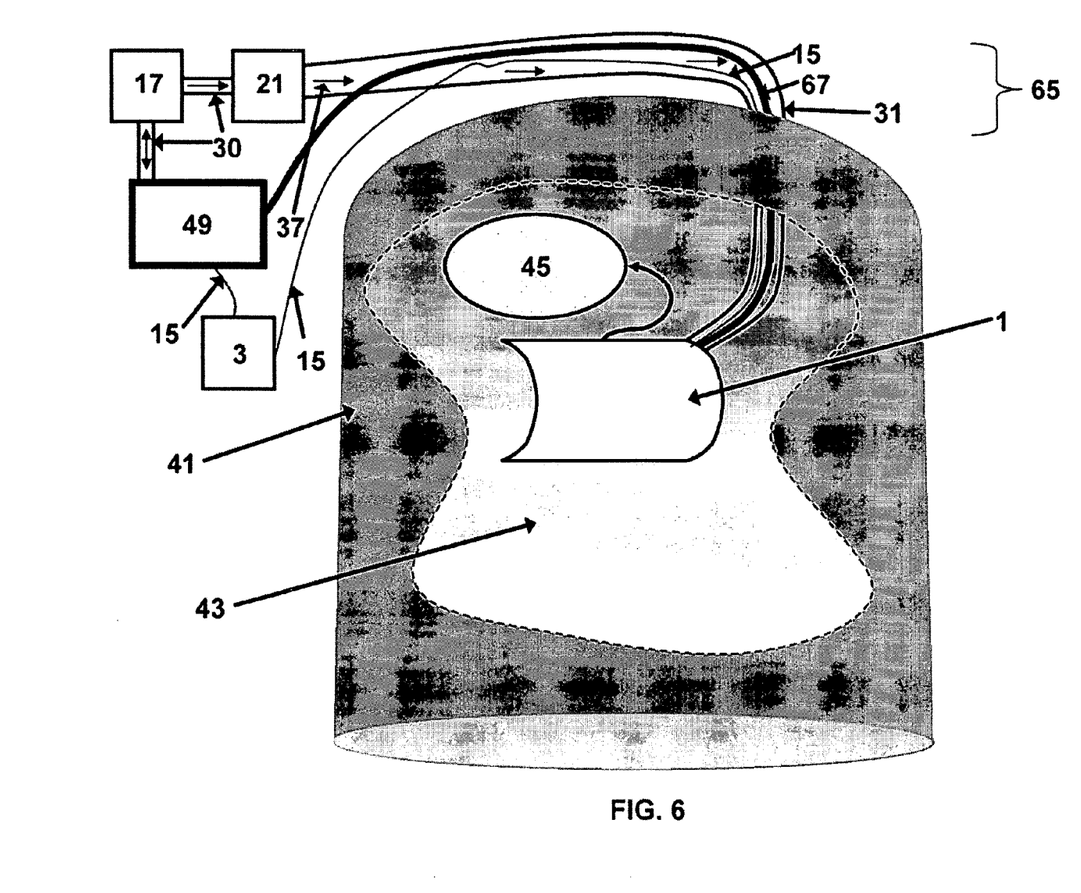
FIG. 6 depicts a cut-out view of an embodiment of the Explosion Proof Vehicle using an Inflatable Float in a Tank having a Volatile Fluid.

FIG. 5 and FIG. 6

FIG. 5 and FIG. 6 depict an embodiment similar to the embodiment shown in FIG. 1 with the addition of an Inflatable Float 45 and a Filling Means 49. As in FIG. 1, the Supply Means 17 supplies the Inert Fluid 37 to the Pressure Controlling means 21, which supplies the Inert Fluid 37 into the Interior 7 of the Outer Shell 5 via one or more Flexible Tubes 31. The Supply Means 17 also supplies the Inert Fluid 37 to the Filling Means 49 through one or more Supply Tubes 30. The Filling Means 49 is connected to the Inflatable Float 45 by one or more Internal Tubes 67 and directs the desired flow of Inert Fluid 37 to the Inflatable Float 45. Preferably, the one or more Internal Tubes 67 pass into the Vehicle 1 through the one or more Flexible Tubes 31. The Filling Means 49 is preferably electrically connected to the Control System 3 by one or more Electrical Conductors 15 and supplies Inert Fluid 37 supplied from the Supply Means 17 to the Inflatable Float 45 at the direction of the Control System 3.

As the Inert Fluid 37 is added or removed from the Inflatable Float 45, the buoyancy of the Vehicle 1 is increased or decreased, respectively, thereby propelling the Vehicle 1 upwards or downwards. In this embodiment, when an upward movement is desired, the Control System 3 preferably signals a Filling Means 49 to supply the Inert Fluid 37, to the Inflatable Float 45.

Filling Means 49

Preferably, the Filling Means 49 directs a Flotation Fluid, preferably the Inert Fluid 37 from the Supply Means 17, into the Inflatable Float 45 as directed by the Control System 3.

In the alternative, the Filling Means 49 may supply a Flotation Fluid that is not necessarily the Inert Fluid 37. The Flotation Fluid is a fluid which is not explosive in the environment provided by the Interior 5 of the Vehicle 1 and will not pose as a serious environmental or safety risk when exposed to the Volatile Fluid 43. Preferably, the Flotation Fluid is a welding gas, a noble gas, or a combination thereof. In a preferred embodiment, the Flotation Fluid is nitrogen or argon, more preferably nitrogen.

One or More Internal Tubes 67

The one or more Internal Tubes 67 allows the transfer of the Inert Fluid 37 from the Filling Means 49 to the Inflatable Float 45. Suitable one or more Internal Tubes 67 include but are not limited to pipes, tubes, channels, etc. . . . The one or more one or more Internal Tubes 67 are preferably made out of plastics, ceramics, metals, or combinations thereof. Preferably, the one or more Internal Tubes 67 are flexible, but alternatively may be one or more rigid tubes having flexible couplings.

Preferably, the one or more Internal Tubes 67 are not exposed to the Volatile Fluid 43 and run interior to the one or more Flexible Tubes 31. In this embodiment, the Vehicle 1 is only tethered to the one or more Flexible Tubes 31 allowing for minimal interference with the maneuverability of the Vehicle 1. Furthermore, if the one or more Internal Tubes 67 are not exposed to the Volatile Fluid 43, but run within the protection of the one or more Flexible Tubes 31, they do not have to be resistant to the Volatile Fluid 43. Preferably, the one or more Internal Tubes 67 are inserted into the one or more Flexible Tubes 31 a non-submersed area 65.

In the alternative, the one or more Internal Tubes 67 may run exterior to the one or more Flexible Tubes 31 and are designed to prevent reaction with the Volatile Fluid 43.

Inflatable Float 45

The Inflatable Float 45 or other Containing Means expands in the Volatile Fluid 43 as it is filled by the Inert Fluid 37. As the Inflatable Float 45 expands, the Vehicle 1 is propelled upwards by the increased buoyancy. Likewise, the Inflatable Float 45 can propel the Vehicle 1 downwards by deflating the Inflatable Float 45 thereby, decreasing the buoyancy of the Inflatable Float 45. Preferably, the Inert Fluid 37 from the Inflatable Float 45 is vented into the Volatile Fluid 43 or more preferably, recycled back into the Filling Means 49.

The Inflatable Float 45 can be very beneficial in situations where the Vehicle 1 can get snagged on roof pillars, piping inlets, or fall into a tank sump. In these situations, it can be extremely difficult to extract the Vehicle 1. By increasing the buoyancy of the Vehicle 1 it can be easily lifted, thereby reducing tension in the Flexible Tubes 31 allowing the Vehicle 1 to be more easily moved.

Figure 7:
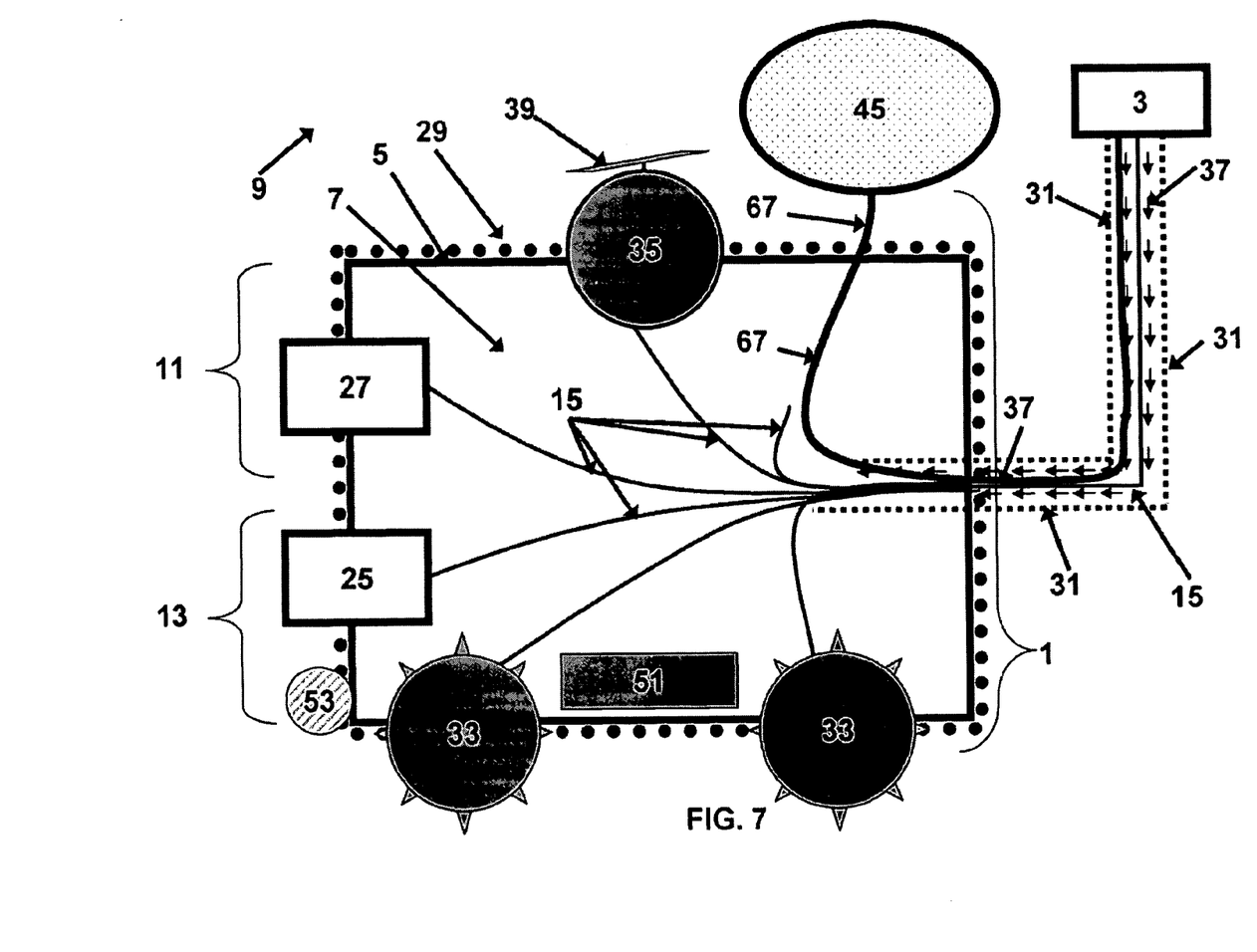
FIG. 7 depicts a block diagram of one embodiment of an Explosion Proof Vehicle using Wheels, one or more Turbines and an Inflatable Float to move the Vehicle.

FIG. 7

In the embodiment shown in FIG. 7 the functions of the Supply Means 17 the Pressure Controlling Means 21 of FIG. 1 are combined into the Control System 3, whereby the Control System 3 supplies an Inert Fluid 37 through one or more Flexible Tubes 31 to the Vehicle 1, while maintaining the pressure of the Interior 7 of the Vehicle 1 above the pressure of the Exterior 9. The Control System 3 also acts as the Filling Means 49 providing the Inert Fluid 37, to the Inflatable Float 45.

The Vehicle 1 in the embodiment shown in FIG. 7, uses the Turbine 35 and Wheels 33 shown in FIG. 4, the Inflatable Float 45 shown in FIG. 5 as well as a Weight 51 connected to the Bottom 13 of the Outer Shell 5 and a Cleaning Brush 53 attached to the front of the Vehicle 1.

Weight 51

The Weight 51 is positioned in the Vehicle 1 to evenly distribute the weight in the Vehicle 1 in order to stabilize the movement of the Vehicle 1. Preferably, the Weight 51 has a high mass to volume ration to minimize the space utilized within the Interior 7 of the Vehicle 1. Preferably, the Weight 51 is lead, iron, steel, or a combination thereof.

Cleaning Brush 53

The Cleaning Brush 53 prevents sediments or other items from interfering with the inspection of the Tank 41 as well as the movement of the Vehicle 1. The Cleaning Brush 53 is constructed from non-sparking materials. In a preferred embodiment the Cleaning Brush 53 is brass bristles attached to the Vehicle 1 with an aluminum bracket and bronze screws.

Figure 8:
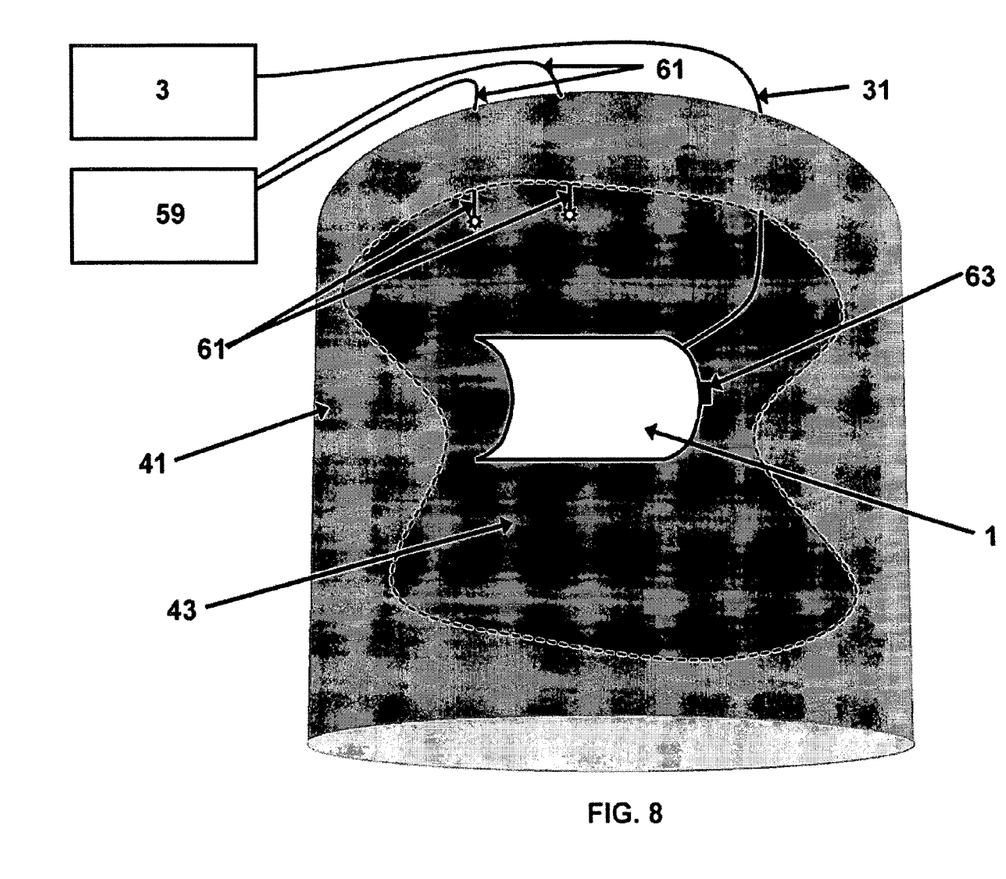
FIG. 8 depicts a cut-out view of a preferred embodiment whereby light is generated outside the Tank and piped to illuminate the Volatile Fluid.

FIG. 8

FIG. 8 depicts a preferred embodiment whereby, the Transmitting Means 25 of the Vehicle 1, such as the Vehicle 1 shown in FIG. 1, FIG. 2, FIG. 4, FIG. 5, and FIG. 7, is one or more Light Sources 59 outside the Tank 41 and away from the presence of the Volatile Fluid 43 and piped into the Tank 41 by one or more Light Pipes 61. As in FIG. 7, the Vehicle 1 is connected to the Control System 3 by one or more Flexible Tubes 31. Preferably, each of the one or more Light Sources 59 is a battery powered sealed light source. Preferably light is generated using one or more incandescent, led or florescent light bulbs.

In this embodiment, the Receiving Means of the Vehicle 1 is preferably one or more Light Sensors 63 on the Vehicle 1 that are used for capturing an image of said illuminated Volatile Fluid 43, said Tank 51, or a combination thereof. Preferably the one or more Light Sensors 63 are used to construct one or more images of the Tank 41.

Each Light Pipe from the one or more Light Pipes 61 is preferably a metal tube having a reflective interior and an exterior coated with a conductive Teflon or plastic.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

All publications and patent documents cited in this application are incorporated by reference in their entirety for all purposes to the same extent as if each individual publication or patent document were so individually denoted.

Any element in a claim that does not explicitly state "means for" performing a specified function, or "step for" performing a specific function, is not to be interpreted as a "means" or "step" clause as specified in 35 U.S.C. §112, ¶ 6. In particular, the use of "step of" in the claims herein is not intended to invoke the provisions of 35 U.S.C. §112, ¶ 6.

The invention claimed is:

1. An apparatus comprising:
   a. a vehicle comprising an outer shell;
   b. said outer shell forming an interior and an exterior;
   c. a sealing means for substantially preventing a fluid from passing into said interior of said outer shell from said exterior of said outer shell;
   d. said outer shell having a top and a bottom;
   e. said interior of said outer shell comprised substantially of an inert fluid and having an interior pressure;
   f. said exterior of said outer shell having an exterior pressure;
   g. said vehicle having a moving means for moving said vehicle;
   h. one or more flexible tubes having a first end and a second end;
   i. a supply means for supplying said interior fluid connected to said second end of said one or more flexible tubes;
   j. said first end of said one or more flexible tubes connected to said vehicle whereby said inert fluid is supplied into said interior of said outer shell from said supply means;
   k. a control system electronically connected to said moving means by one or more electrical conductors;
   l. said one or more electrical conductors passing into said interior of said outer shell through said one or more flexible tubes;
   m. a pressure controlling means for creating and maintaining said interior pressure greater than said exterior pressure connected to said interior of said outer shell;
   n. a transmitting means for transmitting a signal in said exterior;
   o. a receiving means for receiving said signal; and
   p. a spark reducing means for minimizing sparking on said exterior of said outer shell.

2. The apparatus of claim 1 further comprising:
   a. a tank comprising a volatile fluid;
   b. said vehicle submersed in said volatile fluid;
   c. said sealing means comprises a means for substantially preventing said volatile fluid from passing into said interior of said outer shell from said exterior of said outer shell;
   d. said means for moving said vehicle comprises a means for moving said vehicle in said volatile fluid;
   e. each said one or more flexible tubes have a non-submersed portion which is not exposed to said volatile fluid;
   f. said one or more electrical conductors entering one or more flexible tubes from said one or more flexible tubes at said non-submersed portion of said first flexible tube and entering into said interior of said out shell through said first end of said first flexible tube; and g. said control system positioned exterior to said tank.

3. The apparatus of claim 2 whereby:
a. said receiving means comprises:
   i. a sonar transducer flexibly connected to said vehicle and extending outward into said volatile fluid; and
   ii. said sonar transducer electrically connected to said control system; and
b. said transmitting means comprises a means for transmitting sonar.

4. The apparatus of claim 2 whereby:
a. said transmitting means comprises one or more lights optically connected to said volatile fluid; and
b. said receiving means comprises one or more cameras connected to said outer shell.

5. The apparatus of claim 2 whereby said means for moving comprises:
a. one or more wheels rotatably connected to said bottom of said outer shell and extending away from said interior of said outer shell;
b. a means for applying a force to said top of said vehicle having a vector running towards said bottom of said vehicle.

6. The apparatus of claim 5 whereby said means for applying a force comprises a turbine.

7. The apparatus of claim 2 whereby said means for moving comprises:
a. an inflatable float containing a flotation fluid and capable of expanding in said volatile fluid connected to said vehicle; and
b. a means for controlling the inflation of said float connected to said means for containing, whereby said means for containing increases or decreases the buoyancy of said vehicle thereby moving said vehicle upwards and downwards.

8. The apparatus of claim 7 whereby said flotation fluid comprises said inert fluid supplied from said supply means for supplying said inert fluid.

9. The system of claim 8 whereby said means for controlling the inflation of said means for containing is said control system.

10. The apparatus of claim 2 whereby said means for moving comprises a weight connected to said bottom of said outer shell whereby said weight stabilizes the movement of said vehicle.

11. The apparatus of claim 2 whereby:
a. said control system comprises a means for producing a stepped dc voltage signal;
b. said means for moving comprises a stepper motor; and
c. said one or more flexible tubes each comprises a conductive wire having a length greater than 100 feet and a diameter greater than or equal about ½ an inch connected to said control system and said stepper motor.

12. The apparatus of claim 2 further comprising:
a. a cleaning brush attached to said outer shell; and
b. a spark reducing means for reducing sparking from or to said cleaning brush.

13. The apparatus of claim 2 whereby said inert fluid is nitrogen.

14. The apparatus of claim 2 whereby said transmitting means comprises:
a. one or more light sources optically connected to one or more light pipes; and
b. each said light pipe passing into said tank and at least partially illuminating said volatile fluid.

15. The apparatus of claim 2 whereby said receiving means comprises an array of detectors for detecting a signal generated by said transmitting means.

16. The apparatus of claim 2 having a means for substantially preventing said inter fluid from leaving said interior or said outer shell.

17. The apparatus of claim 2 whereby said sealing means is positioned between said interior of said outer shell and said exterior of said outer shell.

18. The apparatus of claim 2 whereby said outer shell prevents said inter fluid from leaving said interior of said outer shell.

19. The apparatus of claim 2:
a. further comprising:
   i. a cleaning brush attached to said outer shell; and
   ii. a sparking means for reducing sparking from or to said cleaning brush; and
b. whereby:
   i. said receiving means comprising:
      1. a sonar transducer flexibly connected to said vehicle and extending outward into said volatile fluid;
      2. said sonar transducer electrically connected to said control system; and
      3. one or more cameras connected to said outer shell;
   ii. said transmitting means comprises:
      1. one or more lights optically connected to said volatile fluid;
      2. one or more light sources optically connected to one or more light pipes;
      3. each said light pip passing into said tank and at least partially illuminating said volatile fluid; and
      4. A means from transmitting sonar;
   iii. said means for moving comprises:
      1. one or more wheels rotatably connected to said bottom of said outer shell and extending away from said interior of said outer shell;
      2. a means for applying a force to said top of said vehicle having a vector running towards said bottom of said vehicle;
      3. said means for applying a force comprises a turbine;
      4. an inflatable float containing a flotation fluid and capable of expanding in said volatile fluid connected to said vehicle;
      5. a means for controlling the inflation of said inflatable float connected to said means for containing increases or decreases the buoyancy of said vehicle thereby moving said vehicle upwards or downwards;
      6. said flotation fluid comprises said inert fluid supplied from said supply means for supplying said inert fluid;
      7. a weight connected to said bottom of said outer shell whereby said weight stabilizes the movement of said vehicle; and
      8. a stepper motor;
   iv. said control system comprises a means for producing a stepped dc voltage signal;
   v. said one or more flexible tubes each comprise a conductive wire having a length greater than or equal to about 100 feet and a diameter greater than or equal to about ½ inch connecter to said control system and said stepper motor;
   vi. said inert fluid is nitrogen; and
   vii. said outer shell prevents said inter fluid from leaving said interior or said outer shell.

20. The apparatus of claim 1, whereby said supply means is exterior to said outer shell.

21. The apparatus of claim 1, further comprising:
   a. said supply means being exterior to said outer shell; and
   b. said means for moving comprising:
      i. an inflatable float containing a flotation fluid and capable of expanding in said volatile fluid connected to said vehicle;
      ii. a means for controlling the inflation of said float connected to said means for containing, whereby said means for containing increases or decreases the buoyancy of said vehicle thereby moving said vehicle upwards and downwards;
      iii. whereby said flotation fluid comprises said inert fluid supplied from said supply means for supplying said inert fluid; and
      iv. said means for controlling the inflation of said means for containing is said control system.

\* \* \* \* \*